United States Patent

Sangokoya

[11] Patent Number: 5,308,815
[45] Date of Patent: May 3, 1994

[54] HETEROGENEOUS METHYLALUMINOXANE CATALYST SYSTEM

[75] Inventor: Samuel A. Sangokoya, Baton Rouge, La.

[73] Assignee: Ethyl Corporation, Richmond, Va.

[21] Appl. No.: 937,778

[22] Filed: Sep. 1, 1992

Related U.S. Application Data

[63] Continuation-in-part of Ser. No. 736,416, Jul. 26, 1991, Pat. No. 5,157,137, and a continuation-in-part of Ser. No. 853,239, Mar. 18, 1992, Pat. No. 5,235,081.

[51] Int. Cl.$^5$ .............................................. C08F 4/64
[52] U.S. Cl. ................................. 502/104; 502/103; 502/117; 502/152; 526/160
[58] Field of Search ............... 502/104, 103, 117, 152

[56] References Cited

U.S. PATENT DOCUMENTS

| | | | |
|---|---|---|---|
| 4,791,180 | 12/1988 | Turner | 502/103 X |
| 5,091,352 | 2/1992 | Kioka et al. | 502/103 |
| 5,157,137 | 10/1992 | Sangokoya | 556/179 |

FOREIGN PATENT DOCUMENTS 0279586  8/1988  European Pat. Off. .

Primary Examiner—Patrick P. Garvin
Attorney, Agent, or Firm—David M. Bunnell

[57] ABSTRACT

A heterogeneous catalyst composition comprising a primary catalyst such as a metallocene and a methylaluminoxane, at least about 10 percent but less than about 40 percent of the total aluminum value in the methylaluminoxane being soluble in toluene at 25° C.

8 Claims, No Drawings

HETEROGENEOUS METHYLALUMINOXANE CATALYST SYSTEM

This application is a continuation-in-part of application Ser. No. 736,416, filed Jul. 26, 1991, now U.S. Pat. No. 5,157,137 and application Ser. No. 853,239, filed Mar. 18, 1992, now U.S. Pat. No. 5,235,081 whose entire teachings are incorporated herein by reference.

This invention relates generally to catalyst systems useful in the dimerization, oligomerization, and polymerization of olefins and more specifically to heterogeneous catalyst systems which contain metallocenes and substantially hydrocarbon solvent insoluble methylaluminoxanes.

Methylaluminoxanes (MAO's) are known to be useful olefin polymerization catalyst components and especially in combination with metallic compounds which serve as the primary catalyst such as, for example, organometallic compounds containing ligands which include at least one cyclopentadienyl moiety, commonly known as metallocenes.

MAO's can be prepared by the partial hydrolysis of trimethylaluminum. In order to control the trimethylaluminum-water reaction, the hydrolysis is carried out at low temperatures in organic solvents. As known in the art, the water can be pre-dispersed or dissolved in an organic solvent, imbibed on a solid support or added in the form of hydrated compound. Because it is generally believed that organic solvent soluble MAO's are necessary for good polymerization activity, the low solubility or insoluble MAO materials in the form of gels or solids, which are formed in the partial hydrolysis reaction, are usually removed from the product by filtration, sometimes preceded by agglomeration or solvent precipitation techniques, and discarded. Suitable processes for gel removal are described, for example, in copending applications Ser. No.'s 736,416, filed Jul. 26, 1991, now U.S. Pat. No. 5,157,137 and 853,239, filed Mar. 18, 1992, now U.S. Pat. No. 5,235,081. The resulting clear solutions are then used to form homogeneous catalyst systems. Heterogeneous catalysts have been prepared by depositing the MAO from solution on inert carriers.

U.S. Pat. No. 5,091,352 describes catalyst components formed by post-reacting MAO solutions with water to form organoaluminum-oxycompounds in which less than 10% of their aluminum values are soluble in benzene at 60° C. This post-reaction inevitably leads to over-hydrolyzed MAO which necessarily contains hydroxide groups which in turn is responsible for cross-linkages leading to the insolubility of the material.

I have now found that the low solubility and/or insoluble portions of the MAO products obtained from the partial hydrolysis of trimethylaluminum with water in combination with primary catalysts such as metallocenes, provide useful heterogeneous, dimerization, oligomerization, and polymerization catalysts. This invention has a distinct advantage for industrial application, in that it provides a use for a by-product of the process for forming soluble MAO used in the well known homogeneous Kaminsky type catalyst systems and, therefore, improves the process economics. The low solubility results primarily from molecular weight differences compared to soluble MAO rather than over-hydrolysis and cross-linking as in the case of U.S. Pat. No. 5,091,352.

In accordance with this invention there is provided a heterogeneous catalyst composition comprising the reaction product of a primary catalyst and a methylaluminoxane, at least about 10 percent but less than about 40 percent of the total amount of aluminum value in said methylaluminoxane being soluble in toluene at 25° C.

Also provided is a process for making a heterogeneous catalyst composition comprising reacting a primary catalyst with a methylaluminoxane where at least about 10 percent but less than about 40 percent of the total aluminum value in said methylaluminoxane is soluble in toluene at 25° C.

Methylaluminoxanes (MAO's) may exist in the form of linear or cyclic polymers. The methylaluminoxanes preferred for use in olefin polymerization catalysts usually contain about 5 to 40 or more of the repeating units:

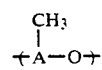

The methylaluminoxanes can contain minor portions of $C_2$ to $C_{10}$ alkyl groups and such materials are included within the term "methylaluminoxanes" as used herein. The methylaluminoxane for use in the heterogeneous catalyst compositions of the invention are believed to be primarily high molecular weight, non-crosslinked methylaluminoxane which has a limited solubility even in aromatic solvents such that at least about 10 percent but less than about 40 percent of the aluminum values are soluble in toluene at 25° C. These methylaluminoxane products contain varying amounts of from about 10 to 30 weight percent aluminum as unreacted trimethylaluminum (TMA) which is believed to be present along with some soluble MAO.

A suitable methylaluminoxane material for use in forming the catalyst of the invention is the by-product from the process described in my co-pending application Ser. No. 853,239. According to this process, an aromatic hydrocarbon solvent solution of MAO, which contains from about 0.5 to 30 weight percent aluminum values, is treated with an aliphatic hydrocarbon solvent to cause the partially soluble and insoluble MAO materials to separate from the solution. The partially soluble and insoluble MAO materials, which are in the form of finely divided particles, are then easily removed by conventional means such as filtration or decantation of the solution.

Preferably, proportions of from about 0.5 to 10 parts by weight of aliphatic hydrocarbon solvent per part by weight of aromatic hydrocarbon solvent solution are employed.

Suitable aliphatic solvents include, but are not limited to, linear and cyclic aliphatic hydrocarbons having from about 5 to 7 carbon atoms, including mixtures thereof. Illustrative examples of such aliphatic solvents include pentane, isopentane, hexane, cyclohexane, heptane, Isopar C and the like.

The fractionation treatment to remove the partially soluble and insoluble MAO materials can be accomplished by adding the aliphatic hydrocarbon solvent to the alkylaluminoxane aromatic solvent solution and stirring vigorously for from about 1 to 15 hours at from ambient temperatures (15°-30° C.) up to the boiling point of the aliphatic hydrocarbon solvent and, preferably, from about 25° to 70° C. The treatment time is not particularly critical and longer or shorter times which are effective to transform the gels and particles of partially insoluble and insoluble MAO materials to an easily filterable form can be used. After the treatment, the methylaluminoxane solids are conveniently removed from the solution by filtration but they can also be removed by any conventional liquid-solid separation technique such as by centrifugation and decanting the liquid.

Another suitable methylaluminoxane material for use in the invention is the by-product obtained from the process described in my co-pending application Ser. No. 736,416, now U.S. Pat. No. 5,157,137. According to this process, cloudy or gelatinous MAO solutions, which contain from about 0.5 to 30 weight percent aluminum values, are treated with an anhydrous salt and/or hydroxide of an alkali or alkaline earth metal in proportions of from about 0.01 to 0.1 moles of metal salt and/or hydroxide per mole of aluminum in the alkylaluminoxane. An effective amount of treating compound is selected to remove the gel and particles.

Suitable anhydrous alkali and alkaline earth metal salts and hydroxides are those which are effective to remove the particulates and gel, but which are substantially inert with respect to the desirable aluminoxanes and any unreacted alkyl aluminum compounds remaining after formation of the aluminoxane.

Specific examples of useful treating compounds include anhydrous LiOH, LiBr, LiCl, NaOH, NaCl, NaBr, and the calcium, magnesium, barium analogs thereof.

The treatment can be accomplished by adding the salt or hydroxide to the alkylaluminoxane solution with stirring for from about 1 to 4 hours at ambient temperatures (15°–30° C.). The time is not particularly critical and longer or shorter times, which are effective to transform the gels and particles of partially insoluble and insoluble MAO materials to an easily filterable form, can be used. Higher or lower temperatures can also be used. Because the heavier metal compounds tend to be more reactive, especially with trimethylaluminum, the treatment of methylaluminoxane with such compounds is preferable done at low temperatures.

After the treatment, the MAO solids, including the treating compound, are conveniently removed from the solution by filtration, but they can also be removed by any conventional liquid-solid separation technique such as by centrifugation and decanting the liquid.

The insoluble and partially soluble MAO products can be used in combination with a primary catalyst to form catalysts useful in the dimerization, oligomerization and polymerization of olefins including both aliphatic olefins such as ethylene, propylene, butenes and the like and aromatic olefins such as styrene and the like or the reaction of other functional groups such as epoxides. Suitable primary catalysts include but are not limited to metal acetylacetonates, metallocenes including derivatives thereof and the like. Preferred primary catalysts for olefin reactions are metallocenes.

The primary metallocene catalysts can be $d^0$ organometallic compounds of a transition metal such as titanium, zirconium or hafnium. As used in this application the term "metallocene" includes metal derivatives which contain at least one cyclopentadienyl moiety. The catalyst structure may be described as metallocene (or bent metallocene in the case of bis-cyclopentadienyl compounds) with ancillary anionic ligands or hydrocarbyl groups, such as metallocenes of the formula $Z_t(\eta^5-R'_nH_mC_5)_sMX_{4-s}$, where R' is a carbon or a carbon and heteroatom (N, O, P, B, Si and the like) containing $C_1$ to $C_6$ alkyl, $C_3$ to $C_{12}$ cycloalkyl or a $C_6$ to $C_{14}$ aryl group. Non-limiting examples of such groups include methyl, ethyl, trimethylsilyl, t-butyl, cyclohexyl, phenyl, 4-methylphenyl, 2,4,6-trimethylphenyl and the like. The R' substituents can be different in type and number on each cyclopentadienyl ring and can form fused cyclic groups attached to the ring. Z is a bridging group between two cyclopentadienyl rings such as silane, phosphine, amine or carbon groups, t is 0 or 1, m and n are integers of 0 to 5, m+n = 5 when t is 0 and 4 when t is 1, s is 1 or 2, M is the transition metal and X is halogen, psuedohalogen, (e.g. a leaving group in nucleophilic substitution such as ester, cyanide, tosylate, triflate, $\beta$-diketonate and the like), hydride or $C_1$ to $C_8$ alkyl. Analogous metallocenes with two different X groups are also effective in the presence of an aluminoxane. Also effective are bimetallic $\mu$-oxo analogues such as $O[ClHf(C_5H_5)_2]_2$ and mono-cyclopentadienyl metal trihalides.

Specific non-limiting examples of primary metallocenes which are useful in forming the heterogeneous catalysts of the invention include bis(cyclopentadienyl)-zirconium dichloride, bis(cyclopentadienyl)hafnium dichloride, bis(pentamethylcyclopentadienyl)hafnium dichloride, bis-(indenyl)hafnium dichloride, bis(methylcyclopentadienyl)hafnium dichloride, racemic and meso dimethylsilanyl bridged bis(methylcyclopentadienyl)hafnium dichloride, bis(cyclopentadienyl)-titanium dichloride, bis(ethylcyclopentadienyl)zirconium dimethyl, bis($\beta$-phenylpropylcyclopentadienyl)zirconium dimethyl, bis(methylcyclo-pentadienyl)zirconium dimethyl, racemic dimethylsilanyl bridged bis(indenyl)hafnium dichloride, racemic ethylene bridged bis(indenyl)zirconium dichloride, ($\eta^5$-indenyl)hafnium trichloride and ($\eta^5$-$C_5Me_5$)hafnium trichloride, and the like.

The heterogeneous catalysts are formed by reacting the methylaluminoxane with the metallocene in proportions of from about 10 to 1000 moles (gram atoms) of aluminum per mole of metallocene in an organic solvent to form solid catalyst products.

The invention is further illustrated by, but is not intended to be limited to, the following examples in which the initial methylaluminoxane was prepared by direct water hydrolysis of a trimethylaluminum solution in toluene.

General Procedures

All experiments were carried out under inert atmosphere conditions, using Schlenk glassware and a vacuum line, in conjunction with a $N_2$-dry box. Solvents were dried using standard methods. Filtration and vacuum distillation were done inside the $N_2$-dry box and distillates were collected in a trap at $-78°$ C.

EXAMPLE 1

A concentrated toluene/MAO solution (50 g, 300 mmol Al) was placed in a reaction vessel. Isopentane (150 g) was added. The mixture was vigorously stirred during a period of about 5 hours. The resulting solution was filtered to remove the precipitated solid which was then washed in toluene and dried under vacuum. The insoluble solid product contained 60% of the original aluminum value.

EXAMPLE 2

Isopentane (200 g) was added to a toluene solution of MAO (50 g, 300 mmol Al) according to the procedure described in Example 1.

EXAMPLE 3

Example 3 was carried out as described in Example 1 except that 300 g of isopentane was employed.

EXAMPLE 4

Concentrated toluene MAO solution (50 g, 300 mmol Al) was placed in a reaction tube. Hexane (150 g) was added and the mixture was magnetically stirred for about 8 hours. The resulting solution was filtered and the insoluble residue was washed with toluene and then vacuum dried.

EXAMPLE 5

Example 5 was performed as described in Example 4 except that 200 g of hexane were added to the MAO solution (50 g).

EXAMPLE 6

Hexane (300 g) was added to MAO solution (50 g, 300 mmol Al) as described in Example 4. The resulting slurry was filtered to give a glassy insoluble solid MAO product, which was washed with toluene and then vacuum dried.

EXAMPLES 7, 8 AND 9

These examples were carried out as described in Example 1 except that, to the MAO solution (50 g, 300 mmol Al) were added, respectively, 150 g, 200 g and 300 g of Isopar C.

EXAMPLE 10

Methylaluminoxane toluene solution (50 g, 300 mmol Al) was placed in a reaction tube. Then, cyclohexane (150 g) was added. The resulting slurry was vigorously stirred at room temperature for about 12 hours. The mixture was filtered. The solid was washed with toluene and then vacuum dried.

EXAMPLES 11 AND 12

MAO in toluene (50 g, 300 mmol Al) was treated with cyclohexane, 200 g and 300 g, respectively. The reactions were carried out as described in Example 10.

Analyses of the insoluble products of Examples 1–12 are given in Table 1.

The previous examples show an average insoluble aluminum recovery of about 45% of the original value. However, if extra toluene is added to the initial 50 g of MAO before the extraction with alkane, a significant decrease of recovered insoluble aluminum value is observed. A similar decrease in insoluble aluminum value is also observed by applying heat to the toluene/alkane slurry of MAO.

Examples 13 to 16 illustrate the former effect while Examples 17 to 21 illustrate the latter effect. The average insoluble aluminum recovery decreased to about 25% of the original aluminum value. These effects could probably be explained by the dynamic equilibrium between the soluble and insoluble methylaluminoxane or more appropriately between TMA and MAO in general. It also appears that the gelatin process is more likely to occur in toluene solution.

EXAMPLES 13

MAO in toluene (50 g, 300 mmol Al) was placed in a reaction tube and then toluene (100 g) and cyclohexane (100 g) were added successively. The mixture was magnetically stirred during a period of about 12 hours. Removal of the precipitated solids, washing with toluene and drying at reduced pressure gave a colorless, free flowing solid.

EXAMPLE 14

Example 14 was carried out as described in Example 13 except that Isopar C replaced cyclohexane.

EXAMPLES 15 AND 16

Examples 15 and 16 were done as described in Example 13, except that the extracting alkane solvents were hexanes and isopentane. The insoluble solids were removed by filtration. They were then vacuum dried to give free flowing glassy solid materials.

Analyses of the insoluble products of Examples 13–16 are given in Table 2.

EXAMPLE 17

To a toluene slurry of MAO (50 g, 300 mmol Al) in a safety screw top reaction tube was added cyclohexane (150 g). The tube was heated in an oil bath at 70° C. for about 4 hours. The tube was brought back into a $N_2$-box where it was filtered. The insoluble solid product was washed with toluene and dried at reduced pressure. The final solid product is colorless and extremely air sensitive. 15% of the original aluminum value was recovered in the solid product.

EXAMPLES 18, 19 AND 20

These Examples were carried out as described in Example 17, except that Isopar C, hexane and isopentane, respectively, were employed as the extracting alkane solvents.

EXAMPLE 21

A MAO slurry in toluene (50 g, 300 mmol Al) was placed in a reaction tube. Additional toluene (100 g) was added followed by isopentane (100 g). The mixture was heated at 70° C. (oil bath) for about 2 hours. The mixture was filtered and the solid residue was vacuum dried and was found to contain 15% of the original aluminum value. This experiment showed that more of the sparingly soluble MAO is dissolved in the presence of additional toluene solvent and heat.

Analytical data for the insoluble solid products of Examples 17–21 are given in Table 3.

EXAMPLE 22

The insoluble products obtained from examples 1 to 12, 13 to 16 and 17 to 21 were combined separately. Each combined product was then allowed to react with bis(cyclopentadienyl) zirconium dichloride in cyclohexane such that the molar ratios Al/Zr were 50, 64 and 74 respectively. The resulting insoluble brick-red products were then used in heterogeneous ethylene polymerization.

The polymerization tests were conducted in a Parr reactor (600 ml) containing toluene (300 ml) at 60 psi (ethylene pressure) and 90° C. during a period of about 10 minutes. The calculated specific activities for the ethylene polymerization reactions were in the range 1.2 to $2.7 \times 10^6$ gPE/mol Zr·Atm·Hr. These values, surprising, compared favorably with values obtained for homogeneous catalysis, using soluble MAO products.

TABLE 1
Fractionation of MAO by Solvent Extraction

| Examples | Reaction Conditions | Product (Wt % Al) | Insoluble Al Value Recovered (Out of 300 mmol) MMol Al | % |
|---|---|---|---|---|
| 1 | MAO/IP/150 | 42.17 | 180 | 60 |
| 2 | MAO/IP/200 | 42.33 | 168 | 56 |
| 3 | MAO/IP/300 | 40.21 | 126 | 42 |
| 4 | MAO/Hex/150 | 40.90 | 141 | 47 |
| 5 | MAO/Hex/200 | 40.99 | 144 | 48 |
| 6 | MAO/Hex/300 | 42.58 | 129 | 43 |
| 7 | MAO/IC/150 | 41.22 | 174 | 58 |
| 8 | MAO/IC/200 | 41.91 | 139 | 45 |
| 9 | MAO/IC/300 | 43.94 | 130 | 43 |
| 10 | MAO/Cyclohex/150 | 40.54 | 138 | 46 |
| 11 | MAO/Cyclohex/100 | 39.81 | 102 | 34 |
| 12 | MAO/Cyclohex/300 | 41.93 | 91 | 31 |

IP = Isopentane; Hex = Hexane; IC = Isopar C and Cyclohex = Cyclohexane
Starting material = 50 g solution (300 mmol Al)
MAO/IP/150 = Isopentane (150 g) added to 50 g MAO solution

TABLE 2
Effect of Additional Toluene Solvent on Insoluble Al Recovered

| Examples | Reaction Conditions | Product (Wt % Al) | Insoluble Al Value Recovered (Out of 300 mmol) MMol |
|---|---|---|---|
| 13 | MAO/Tol/Cyclohex (100/100) | 41.35 | 68 23 |
| 14 | MAO/Tol/IC (100/100) | 41.58 | 93 31 |
| 15 | MAO/Tol/Hex (100/100) | 41.63 | 111 37 |
| 16 | MAO/Tol/IP (100/100) | 41.47 | 95 32 |

Hex = Hexane; IC = Isopar C; IP = Isopentane
Starting material = (50 g solution, 300 mmol Al)
(50/150) = 50 g toluene and 150 g alkane
Al recovery without additional toluene was approx. 50%

TABLE 3
Effect of Heating on Insoluble Al Recovered

| Examples | Reaction Conditions | Product (Wt % Al) | Insoluble Al Value Recovered (Out of 300 mmol) MMol Al |
|---|---|---|---|
| 17 | MAO/Tol/Cyclohex (50/150) Heat | 40.62 | 45 15 |
| 18 | MAO/Tol/IC (50/150) Heat | 40.53 | 86 29 |
| 19 | MAO/Tol/Hex (50/150) Heat | 40.64 | 121 41 |
| 20 | MAO/Tol/IP (50/150) Heat | 40.82 | 139 46 |
| 21 | MAO/Tol/IP (100/100) | 42.95 | 44 15 |

Hex = Hexane; IC = Isopar C; IP = Isopentane
Starting material = (50 g solution, 300 mmol Al)
(50/150) = 50 g toluene and 150 g alkane

Solubility Determination

Solid MAO product obtained as the insoluble residue of solvent fractionation (5 g) containing about 85 mmol of aluminum (46 wt % Al) is slurried with 100 grams of dry toluene (100 g). The mixture is stirred at room temperature for about 4 hours. Typically after filtration, the liquid filtrate is found to contain 10–30 mmoles of aluminum which corresponds to about 12–35 percent of the original aluminum value.

What is claimed is:

1. A heterogeneous catalyst composition comprising the reaction product of a metallocene catalyst and a methylaluminoxane, at least about 10 percent but less than about 40 percent of the total aluminum value in said methylaluminoxane being soluble in toluene at 25° C., said methylaluminoxane being the partially soluble and insoluble methylaluminoxane materials prepared by the fractionation of a methylaluminoxane solution by adding an aliphatic solvent to a methylaluminoxane solution in an aromatic solvent so as to cause said partially soluble and insoluble methylaluminoxane materials to separate as a solid from said solution.

2. The catalyst composition according to claim 1 wherein said metallocene is a transition metal compound.

3. The catalyst composition according to claim 2 wherein the transition metal is selected from the group consisting of titanium, zirconium and hafnium.

4. The catalyst composition of claim 1 wherein said catalyst composition contains from about 10 to 1000 moles of aluminum per mole of metallocene.

5. A process for making a heterogeneous catalyst composition comprising reacting a metallocene catalyst with a methylaluminoxane, at least about 10 percent but less than about 40 percent of the total aluminum value in said methylaluminoxane being soluble in toluene at 25° C., said methylaluminoxane being the partially soluble and insoluble methylaluminoxane materials prepared by the fractionation of a methylaluminoxane solution by adding an aliphatic solvent to a methylaluminoxane solution in an aromatic solvent so as to cause said partially soluble and insoluble methylaluminoxane materials to separate as a solid from said solution.

6. The process according to claim 5 wherein said metallocene is a transition metal compound.

7. The process according to claim 6 wherein said transition metal is selected from the group consisting of titanium, zirconium and hafnium.

8. The process according to claim 5 wherein said catalyst composition contains from about 10 to 1000 moles of aluminum per mole of catalyst.

* * * * *